US011745028B2

(12) United States Patent
Majcher et al.

(10) Patent No.: US 11,745,028 B2
(45) Date of Patent: Sep. 5, 2023

(54) SYSTEMS AND METHODS FOR DESIGN AND FABRICATION OF SURFACE BRACHYTHERAPY APPLICATORS

(71) Applicant: ADAPTIIV MEDICAL TECHNOLOGIES INC., Halifax (CA)

(72) Inventors: Christopher Majcher, Dartmouth (CA); Borko Basaric, Halifax (CA); James L. Robar, Halifax (CA)

(73) Assignee: ADAPTIIV MEDICAL TECHNOLOGIES, INC., Hallifax (CA)

( * ) Notice: Subject to any disclaimer, the term of this patent is extended or adjusted under 35 U.S.C. 154(b) by 612 days.

(21) Appl. No.: 16/868,021

(22) Filed: May 6, 2020

(65) Prior Publication Data

US 2021/0016106 A1 Jan. 21, 2021

Related U.S. Application Data

(60) Provisional application No. 62/875,775, filed on Jul. 18, 2019.

(51) Int. Cl.
*A61N 5/10* (2006.01)
*G06F 30/10* (2020.01)
(Continued)

(52) U.S. Cl.
CPC .......... *A61N 5/1028* (2013.01); *B29C 64/386* (2017.08); *B33Y 50/00* (2014.12);
(Continued)

(58) Field of Classification Search
CPC ...... A61N 5/1028–1029; A61N 5/1001–1029; A61N 2005/1003–1025; B29L 2031/753–7536
See application file for complete search history.

(56) References Cited

U.S. PATENT DOCUMENTS

| 9,990,765 B2 | 6/2018 | Ju et al. |
| 10,286,197 B2 | 5/2019 | Pouliot et al. |

(Continued)

FOREIGN PATENT DOCUMENTS

| WO | 2015013716 A1 | 1/2015 |
| WO | 2017200298 A1 | 11/2017 |

OTHER PUBLICATIONS

Clarke, Scott Alan. 3D Printed Surface Applicators for High Dose Rate Brachytherapy. Masters Thesis. Dalhousie University, Halifax Nova Scotia, Aug. 2016. (Year: 2016).*

(Continued)

*Primary Examiner* — Thaddeus B Cox
(74) *Attorney, Agent, or Firm* — HILL & SCHUMACHER

(57) ABSTRACT

Systems and methods are provided for generating surface brachytherapy applicators in which catheter channel trajectories are generated laterally from both sides of a cut plane bisecting an initial model of the surface brachytherapy applicator model, thereby mitigating the effects of patient-surface-induced curvature. The catheter channels may be defined based on catheter channel trajectories that are spatially distributed, relative to the cut plane, on both sides of the cut plane, and spatially offset relative to a patient-facing surface of the surface brachytherapy applicator model. In some example embodiments, catheter channel trajectories are spaced relative to the cut plane such that neighbouring catheter channel trajectories are evenly spaced along a set of contours. Prior to fabrication, the local radius of curvature of catheter channels may be adjusted in a manual or automated manner to exceed a threshold.

20 Claims, 8 Drawing Sheets

```
┌─────────────────────────────────────┐
│   OBTAIN INITIAL DIGITAL SURFACE    │─── 200
│  BRACHYTHERAPY APPLICATOR MODEL     │
└─────────────────────────────────────┘
                  │
                  ▼
┌─────────────────────────────────────┐
│   IDENTIFY CUT PLANE FOR BISECTING  │
│   THE INITIAL DIGITAL SURFACE       │─── 205
│   BRACHYTHERAPY APPLICATOR MODEL    │
└─────────────────────────────────────┘
                  │
                  ▼
┌─────────────────────────────────────┐
│   PROCESS INITIAL DIGITAL SURFACE   │
│   BRACHYTHERAPY APPLICATOR MODEL TO │
│   GENERATE AND SPATIALLY DISTRIBUTE,│
│   RELATIVE TO CUT PLANE, FIRST SET  │─── 210
│   OF CATHETER CHANNELS ON FIRST     │
│   SIDE OF CUT PLANE AND SECOND SET  │
│   OF CATHETER CHANNELS ON SECOND    │
│   SIDE OF CUT PLANE                 │
└─────────────────────────────────────┘
```

(51) Int. Cl.
*B33Y 80/00* (2015.01)
*B33Y 50/00* (2015.01)
*B29C 64/386* (2017.01)
*B29L 31/00* (2006.01)
*G06Q 50/04* (2012.01)

(52) U.S. Cl.
CPC ...... *G06F 30/10* (2020.01); *A61N 2005/1021* (2013.01); *B29L 2031/753* (2013.01); *B33Y 80/00* (2014.12); *G06Q 50/04* (2013.01)

(56) References Cited

U.S. PATENT DOCUMENTS

| | | | |
|---|---|---|---|
| 2015/0265849 A1* | 9/2015 | Krechting | A61B 34/10 264/129 |
| 2016/0093100 A1* | 3/2016 | Ju | G05B 19/4099 700/98 |
| 2018/0001547 A1 | 1/2018 | Cuypers et al. | |
| 2018/0318603 A1 | 11/2018 | Park et al. | |

OTHER PUBLICATIONS

Clarke et al., Med. Phys. 43, 4934-4935 (2016).
Harris et al., Australas. Phys. Eng. Sci. Med. 38, 399-412 (2015).
Yeo, et al., Application of 3D printed surface mould for skin cancer brachytherapy, 27th Annual Scientific Meeting Australasian Brachytherapy Group (2018).
Arenas et al., J. Contemp. Brachy. 9, 270-276, (2017).
Scott Clarke, Additive Manufacturing and 3D printing presentation Halifax Jun. 2018.
Clarke, PhD Thesis, 3D Printed Surface Applicators for High Dose Rate Brachytherapy, Dalhousie University, (2016).
Cumming et al., 3D Printed Patient-specific Surface Mould Applicators for Brachytherapy Treatment of Superficial Lesions, AMOS 2014 AAPM Annual Meeting (2014).
Jones et al., Brachyther. 16, 409-414 (2017).
Cunha et al., J. Appl. Clin. Med. Phys. 16, 246-253 (2015).
Vavassori et al., Dosimetric evaluation of 3D printed applicators for High Dose Rate brachytherapy, Physica Medica 32, S14-S15 (2016).
Schumacher et al., 3D-printed surface mould applicator for high-dose-rate brachytherapy, SPIE Medical Imaging (2015).
Cumming et al., 3D Printed Patient-Specific Surface Mould Applicators for Brachytherapy Treatment of Superficial Lesions, Med. Phys. 41, 222-222 (2014).
Zhao et al., Medical Dosimetry 42, 150-155 (2017).
International Search Report PCT/CA2020/050608 dated Aug. 31, 2020.
Ian Cumming, Chandra Joshi, Andras Lasso, Adam Rankin, Conrad Falkson, L. John Schreiner, Gabor Fichtinger, "3D Printed Patient-specific Surface Mould Applicators for Brachytherapy Treatment of Superficial Lesions". Laboratory for Percutaneous Surgery, School of Computing, Queen's University, Kingston, Ontario, Canada; CCSEO, Kingston General Hospital and Department of Oncology, Queen's University, Kingston, Ontario, Canada, Mar. 3, 2014.
Emma-Louise Jones, Anna Tonino Baldion, Christopher Thomas, Tom Burrows, Nick Byrne, Victoria Newton, Sarah Aldridge, "Introduction of novel 3D-printed superficial applicators for high-dose-rate skin brachytherapy". Brachytherapy, 2017, vol. vol. 16, Issue 2, pp. 409-414, ISSN 1538-4721.
Adaptiiv Medical Technologies Inc., "Brachytherapy Applicator—Adaptiiv". Youtube, Aug. 28, 2018 [online] [retrieved on Jul. 30, 2020 (Jul. 30, 2020)]. Retrieved from the Internet: https://www.youtube.com/watch?v=6Wv460IAHEQ.

* cited by examiner

SYSTEMS AND METHODS FOR DESIGN AND FABRICATION OF SURFACE BRACHYTHERAPY APPLICATORS

CROSS-REFERENCE TO RELATED APPLICATION

This application claims priority to U.S. Provisional Patent Application No. 62/875,775, titled "SYSTEMS AND METHODS FOR DESIGN AND FABRICATION OF SURFACE BRACHYTHERAPY APPLICATORS" and filed on Jul. 18, 2019, the entire contents of which is incorporated herein by reference.

BACKGROUND

The present disclosure relates to surface brachytherapy applicators and the design and fabrication thereof.

Radiation therapy is a cancer treatment modality used on approximately 50% of all cancer patients. The modality employs ionizing radiation to eliminate cancer cells utilizing sophisticated imaging data-based computer models for planning the adequate dose to be delivered to the patient in form of precise irradiation of the planning target volume (PTV) and at the same time minimizing damaging effects to the organs at risk. A certain percentage of all radiation therapy treatments requires a superficial deposition of dose into the patient tissue.

Skin cancer is the most usual type of cancer affecting the world population with the main three types being squamous cell carcinoma affecting approximately 20% of all skin cancer patients, basal cell carcinoma affecting 75-80%, and melanoma. As most of skin cancer patients are prescribed with a radiation treatment, they will receive either megavoltage electron therapy, orthovoltage therapy, or brachytherapy which ensure the superficial delivery of radiation to the cancerous tissue while sparing as much of the underlying tissue as possible. The primary benefit of using brachytherapy over external beam therapy (MV photons, orthovoltage photons, or electrons) is the distinct dose distribution coming from the radioactive source governed primarily by the inverse square law where the dose is being delivered in close proximity to the radiation source, meaning maximized sparing of the surrounding underlying tissue can be achieved.

The general concept of brachytherapy consists of introducing a sealed radioactive source (or seed) into close proximity of a cancer tissue allowing a natural radioactive decay of the source atoms to irradiate the target. High-dose-rate (HDR) brachytherapy uses most commonly Iridium-192 (Ir-192) sealed sources with activities greater than 12 Gy/hour to treat patients. Ir-192 decays with an average energy of 380 keV and a half-live of 73.8 days. The source is confined in the radiation protected container called "afterloader" which determines the position of the source within the catheter (applicator), dwell times at each position, and provides shielding for clinical staff when not in use.

As a protection mechanism, the afterloader typically contains a dummy (non-radioactive source) which has similar dimensions to the real source which purpose is twofold: the dummy is ensuring there are no physical obstructions for the real radiation source to go through tube guidelines/catheters/applicators and at the same time it is measuring the overall pathlength of the source ensuring the correct dwell positions are to be used. Any obstruction in the pathlength of the source may result in the source being stuck within the catheter/applicator, thus creating an emergency situation that could potentially give unnecessary overexposure to the patient and staff. Once the dummy source check is successful, a treatment begins with a computer-guided radioactive source going into well-defined dwell positions in order to deliver a prescribed dose to the patient. Once the treatment is over, the source retracts back into the afterloader which acts as a protecting safe from ionizing radiation produced by Ir-192 nuclear decay.

Devices that are used to fix the source trajectory to the patient are generally referred to as brachytherapy applicators. Brachytherapy applicators ensure that the radioactive source is placed at a prescribed (usually very close) distance from the tumor site. As for the superficial use in brachytherapy, various surface brachytherapy applicators have been designed to ensure that the source is being kept at a precise distance from the patient's skin. HDR brachytherapy uses surface molds, various types of applicators and thermoplastic masks for treating superficial lesions extending a few millimeters below the surface of the skin. Basal cell carcinoma and squamous cell carcinoma are often successfully treated with this technique resulting in excellent tumor control and few cosmetic defects. Common HDR brachytherapy skin applicators include "Leipzig" or "Valencia" applicators used for smaller tumor targets up to 2-3 cm and Freiburg Flap, wax molds and thermoplastic masks used for larger tumor targets.

As the design of the surface brachytherapy applicator for larger tumors is considered the most manual-labor-involved technique requiring substantial technical skills of the staff comparing to any other radiation therapy modality, certain difficulties occur with the present designs of surface brachytherapy applicators. For example, patient-to-patient reproducibility of source trajectories heavily depends on the manual technical skills of staff involved in the production of the applicator. Features that are mostly affected include trajectory source-to-surface distance which directly influences the dose fall off governed by the inverse square law and inter-trajectory distance constancy which can further affect the dose distribution within the patient. Another challenge with conventional surface brachytherapy applicator design and fabrication techniques is that extreme curvatures of the source trajectories cannot be efficiently mitigated.

SUMMARY

Systems and methods are provided for generating surface brachytherapy applicators in which catheter channel trajectories are generated laterally from both sides of a cut plane bisecting an initial model of the surface brachytherapy applicator model, thereby mitigating the effects of patient-surface-induced curvature. The catheter channels may be defined based on catheter channel trajectories that are spatially distributed, relative to the cut plane, on both sides of the cut plane, and spatially offset relative to a patient-facing surface of the surface brachytherapy applicator model. In some example embodiments, catheter channel trajectories are spaced relative to the cut plane such that neighbouring catheter channel trajectories are evenly spaced along a set of contours. Prior to fabrication, the local radius of curvature of catheter channels may be adjusted in a manual or automated manner to exceed a threshold.

Accordingly, in a first aspect, there is provided a method of generating a digital model of a custom surface brachytherapy applicator, the method comprising:

a) obtaining an initial digital surface brachytherapy applicator model, wherein the initial digital surface brachytherapy applicator model comprises a patient-facing surface;

b) identifying a cut plane for bisecting the initial digital surface brachytherapy applicator model;

c) processing the initial digital surface brachytherapy applicator model to incorporate a plurality of catheter channels, thereby obtaining a modified digital surface brachytherapy applicator model, wherein the plurality of catheter channels are incorporated such that:

a first set of catheter channels are spatially distributed, relative to the cut plane, on a first side of the cut plane; and a second set of catheter channels are spatially distributed, relative to the cut plane, on a second side of the cut plane.

In another aspect, there is provided a system for generating a digital model of a custom surface brachytherapy applicator, the system comprising:

a processing system comprising at least one processor and memory operatively coupled to the at least one processor, wherein the memory comprises instructions executable by the at least one processor for performing operations comprising:

obtaining an initial digital surface brachytherapy applicator model, wherein the initial digital surface brachytherapy applicator model comprises a patient-facing surface;

identifying a cut plane for bisecting the initial digital surface brachytherapy applicator model;

processing the initial digital surface brachytherapy applicator model to incorporate a plurality of catheter channels, thereby obtaining a modified digital surface brachytherapy applicator model, wherein the plurality of catheter channels are incorporated such that:

a first set of catheter channels are spatially distributed, relative to the cut plane, on a first side of the cut plane; and a second set of catheter channels are spatially distributed, relative to the cut plane, on a second side of the cut plane.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1A:
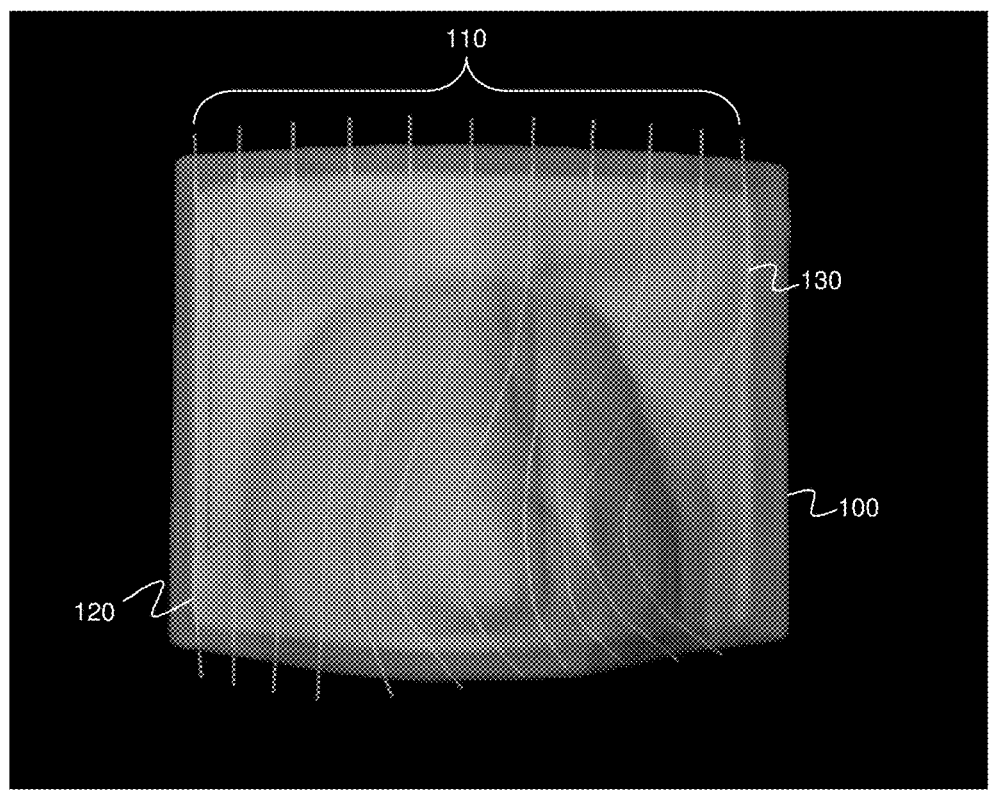
FIG. 1A shows an example method in which catheter trajectories are arranged across the surface brachytherapy applicator from one side of the applicator, resulting in the catheter trajectories on the far right hand-side becoming more and more warped, following the patient curvature, which can potentially impede catheter placement and affect the homogeneity of the dose in the treatment plan.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Various example embodiments of the present disclosure address shortcomings in the art of surface brachytherapy applicator design by providing automated design methods that mitigate the effect of patient anatomical curvature on the curvature of the catheter channels. As explained above, a significant problem in conventional surface brachytherapy applicator design is the highly curved catheter channels that can result from the curvature of the patient anatomical surface. As will be explained further below, surface brachytherapy applicator design methods can result in highly curved catheter channels due to the accumulation of curvature as the catheter channels sequentially generated from one side of the surface brachytherapy applicator to another side of the surface brachytherapy applicator. Such highly curved catheter channels can be problematic as the channel curvature can impede catheter placement, especially when the radius of curvature of the channel is less than a prescribed minimum radius of curvature of the catheter, potentially affecting the homogeneity of the dose in the treatment plan and presenting risk to the patient due to unsafe radiation exposure and/or failure to implement a prescribed radiotherapy plan.

The present inventors sought to overcome these problems in surface brachytherapy applicator design by developing methods that would facilitate the generation of catheter channels with reduced curvature. The inventors, understanding the effect of the curvature of the patient surface on the additive warping of catheter channels when channels are sequentially generated across the surface brachytherapy applicator, developed new methods based on the use of a cut plane. These new methods have been shown to significantly reduce the patient-surface-induced curvature of catheter channels.

Accordingly, in some example embodiments of the present disclosure, the curvature of catheter channels can be reduced by employing a method in which catheter channel trajectories are generated laterally from both sides of a cut plane, where the cut plane bisects the initial model of the surface brachytherapy applicator model (the initial model being absent of catheter trajectories). When the catheter channel trajectories are sequentially (serially) generated from both sides of the cut plane that resides within the initial model of the surface brachytherapy applicator, as opposed to being generated from a location that resides at an outer edge or side of the initial model of the surface brachytherapy applicator, the patient-surface-induced curvature (anatomically-induced curvature) is only accumulated across a subset of the initial model of the surface brachytherapy applicator, and the outer catheter channels (residing adjacent to the edge of the surface brachytherapy applicator) have less accumulated curvature and are thus less likely to exhibit a radius of curvature that would impede or prohibit the passage of a catheter.

In one example implementation, the present methods for the generation of a custom brachytherapy applicator may be incorporated into standard radiotherapy clinical workflow as follows. Firstly, volumetric images (e.g. CT DICOM images) of a patient are obtained and exported to a treatment planning system. The treatment planning system may be employed to generate and export various RT structures, such as, but not limited to, the skin surface of a patient, the planning target volume (PTV) and an initial model of the surface brachytherapy applicator (the latter may be generated, for example, as a "bolus" structure within the treatment planning system). The volumetric images and RT structures may be referred to, for example, as a "patient dataset".

As explained below, a user interface may be employed to enable to selection and importation of the RT structures and the definition of surface brachytherapy applicator parameters such as, but not limited to, the number of catheter channels (conduits, lumens), the orientation of the catheter channels, the radius of the catheter channels, the source-to-surface distance and inter-channel distance. The patient dataset and the surface brachytherapy applicator parameters may then be processed, according to the present example methods in which catheter channels are generated relative to a cut plane, to generate a modified surface brachytherapy applicator model having internal catheter channels. The user interface may be configured to permit the adjustment of the curvature of one or more of the catheter channels.

The resulting modified surface brachytherapy applicator model may then be fabricated, for example, using a rapid prototyping method such as three-dimensional (3D) printing. After having fabricated the surface brachytherapy applicator, volumetric images of the patient may be obtained with the fabricated surface brachytherapy applicator placed on the treatment area, and the acquired volumetric images may be sent to a treatment planning system for delineation and dose calculation, resulting in a treatment plan customized to the fabricated surface brachytherapy applicator. The patient may then be treated according to the treatment plan with the fabricated surface brachytherapy applicator.

Figure 1B:
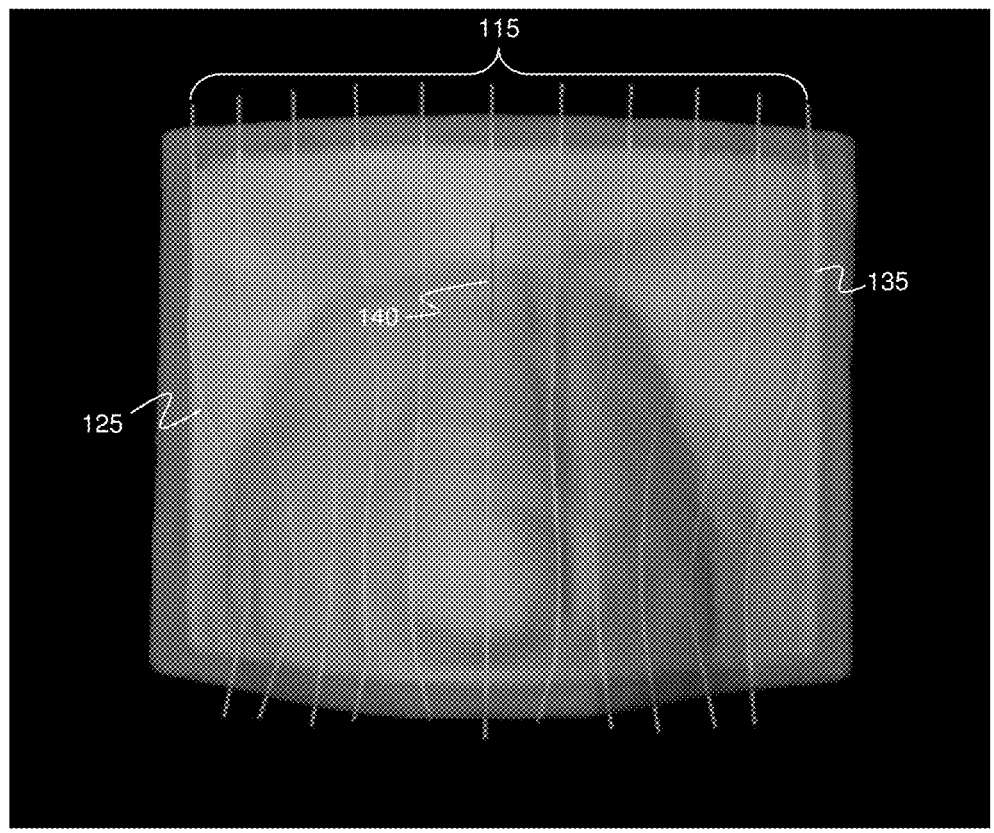
FIG. 1B shows another example method of spatially distributing catheter channel trajectories relative to a cut plane that is positioned along the most curved part of the surface brachytherapy applicator (the nose). As can be clearly seen, this cut plane placement introduces minimal warping of the outside lateral trajectories, making it the best choice for treatment planning in terms of dose shaping and homogeneity.

FIGS. 1A and 1B show an example a surface brachytherapy applicator and illustrate the effect of patient surface curvature on the curvature of catheter channels generated according to different methods. The example surface brachytherapy applicator 100 shown in the figures is designed to be placed over a patient's nose, with the nose shape clearly seen in the center of the surface brachytherapy applicator. FIG. 1A illustrates one example method of generating catheter channel trajectories in which the catheter channel trajectories are sequentially defined, with an equal inter-catheter-channel spacing, from the left side of the surface brachytherapy applicator 100 to the right side of the surface brachytherapy applicator. The set of catheter channel trajectories are shown by the lines 110, and these lines represent the location of catheter channels formed within the surface brachytherapy applicator.

The first catheter channel trajectory 120 is defined on the far left-hand side of the surface brachytherapy applicator 100 and extends in a vertical direction according to a preferred direction of the catheter channels. As the additional catheter channel trajectories are subsequently defined, such that the catheter channel trajectories are equally spaced along the patient-facing side of the surface brachytherapy applicator 100, the additional catheter trajectories become increasing warped due to the high curvature of the patient in the nose region. The final catheter channel trajectory 130, shown near the far-right side of the surface brachytherapy applicator 100, has the largest curvature due to the accumulation of the patient surface curvature during the sequential forming of the equally spaced catheter channel trajectories.

FIG. 1B illustrates an alternative and improved method of defining and generating catheter channel trajectories. Unlike FIG. 1A, in which the catheter channel trajectories were sequentially generated from one side of the surface brachytherapy applicator, the method illustrated in FIG. 1B employs a cut plane, schematically shown at 140, to bisect the surface brachytherapy applicator into two distinct portions. The cut plane 140 is employed during the generation of the catheter channel trajectories such that the catheter channel trajectories are defined and spaced relative to the cut plane on both sides of the cut plane. As can be seen in FIG. 1B, the present example embodiment involves the use of the cut plane to define a central catheter channel trajectory (shown aligned with the cut plane 140) along a preferred direction (defined by the cut plane, thereby providing an orientation of the catheter channel trajectories), with additional catheter channel trajectories spaced laterally relative to the cut plane on each side of the cut plane.

This method of generating catheter channel trajectories based on a cut plane located within the surface brachytherapy applicator results in less accumulation of patient-induced curvature as the catheter channel trajectories are defined relative to the cut plane, resulting in catheter channel trajectories with less curvature and thus a larger minimum radius of curvature. This reduction in catheter channel curvature can be clearly seen, for example, by the outer catheter channel trajectories 125 and 135 in FIG. 1B, both of which have less curvature than the highly curved catheter channel trajectory 130 on the far-right side of the surface brachytherapy applicator of FIG. 1A. In effect, by selecting an internal location for generating the catheter channel trajectories, the induced curvature is more evenly spread across the set of catheter channel trajectories 115.

Figure 2:
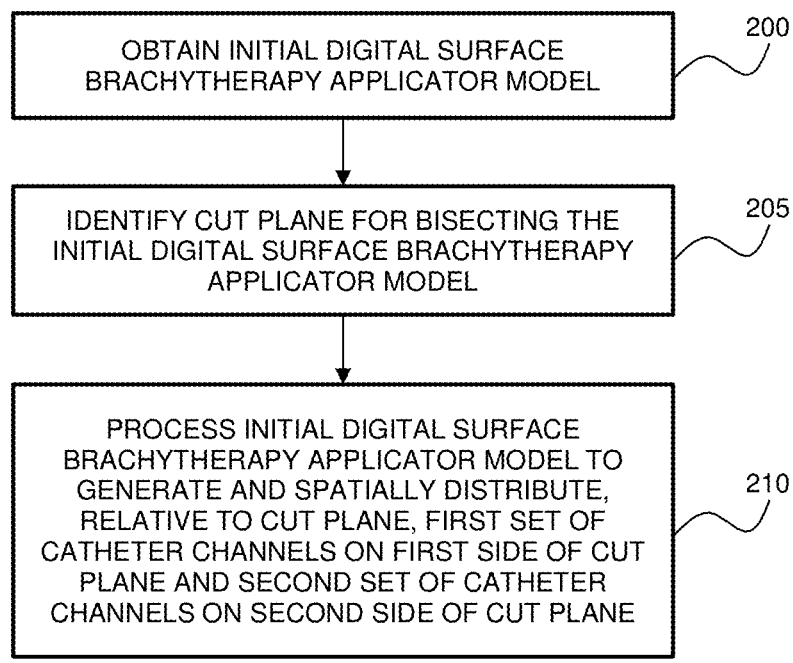
FIG. 2 is a flow chart illustrating an example method of generating a digital model of a custom surface brachytherapy applicator.

Referring now to FIG. 2, a flow chart is provided that illustrates an example method of generating a digital model of a custom surface brachytherapy applicator. The example method involves the modification of an initial digital surface brachytherapy applicator model that is initially generated absent of catheter tunnels. The initial digital surface brachytherapy applicator model is obtained in step 200 of FIG. 2. The initial digital surface brachytherapy applicator model may be defined, for example, in a treatment planning system and subsequently imported as an RT structure into an integrated or separate surface brachytherapy applicator design model software system. For example, in a treatment planning system, one can define the applicator structure using a "create bolus" option which creates an RT structure that fully conforms to the body contour of patient with a user-defined thickness. The extent (size) of the bolus can be manually defined in axial/sagittal/coronal viewing windows by manually dragging the bounding box of the structure. This results in an RT structure of defined size and thickness, fully conforming to the patient body contour. The size and shape of the applicator (bolus-like applicator) will typically depend on the position and size of the PTV or generally on the tumour target and, and these aspects are often considered when creating the initial surface brachytherapy applicator model.

A cut plane is then defined that bisects the initial digital surface brachytherapy applicator into two separate portions, as shown at 205. In some example embodiments, the cut plane may be user-defined, while in other example embodiments, the determination of a suitable location of the cut plane may be at least partially automated. Example methods of selection of the cut plane are described in further detail below.

The cut plane is employed to process the initial digital surface brachytherapy applicator model to determine suitable locations for the inclusion of a set of catheter channels. The catheter channels are spatially distributed relative to the cut plane, such that the impact of patient curvature on the catheter channels does not continuously and increasingly accrue across the full set of catheter channels. A first set of catheter channels are generated and spatially distributed relative to the cut plane on a first side of the cut plane, while a second set of catheter channels are generated and spatially distributed relative to the cut plane on a second side of the cut plane, as shown at 210.

Parameters such as, but not limited to, the cut plane location, the number of catheter channels, the diameter (or radius) of the catheter channels, the spatial offset of the catheter channels relative to the patient-facing surface of the surface brachytherapy applicator, and an initial direction associated with the generation of catheter channels, may be fully or partially defined by a user, for example, via a user interface. In some example implementations, one or more of such parameters may be be pre-defined or automatically generated.

The catheter channels may be generated, for example, by defining a plurality of catheter trajectories that include a first set of catheter trajectories spatially distributed, relative to the cut plane, on the first side of the cut plane and a second set of catheter trajectories spatially distributed, relative to the cut plane, on the second side of the cut plane. The plurality of catheter trajectories may be defined such that they reside within the initial digital surface brachytherapy applicator model at a location corresponding to an internal offset surface that is recessed, within the initial digital surface brachytherapy applicator model, relative to the patient-facing surface, by a prescribed offset, such that the plurality of catheter trajectories reside within the initial digital surface brachytherapy applicator model (i.e. each catheter trajectory is offset, along its length, in a direction parallel to a local surface normal of the patient-facing surface, by the prescribed offset). The initial digital surface brachytherapy applicator model may then be modified to incorporate the plurality of catheter channels such that each catheter channel has a longitudinal axis defined by a respective catheter trajectory. Various example methods of spatially distributing the first and second sets of catheter trajectories, relative to the cut plane, are described below.

In one example implementation, the first set of catheter trajectories may be defined, relative to the cut plane, by defining an initial first catheter trajectory that resides within the internal offset surface adjacent to the cut plane, on the first side of the cut plane, and is spatially offset, along a length thereof, from the cut plane, by a first offset measure defined within the internal offset surface. A plurality of additional first catheter trajectories may then be defined on the first side of the cut plane, such that each pair of neighbouring first catheter trajectories are spatially offset, within the internal offset surface, by a constant inter-channel separation measure.

Likewise, the second set of catheter trajectories are defined, relative to the cut plane, by defining an initial second catheter trajectory that resides within the internal offset surface adjacent to the cut plane, on the second side of the cut plane, and is spatially offset, along a length thereof, from the cut plane by a second offset measure defined within the internal offset surface, and further defining a plurality of additional second catheter trajectories on the second side of the cut plane, such that each pair of neighbouring second catheter trajectories are spatially offset, within the internal offset surface, by the constant inter-channel separation measure.

The first and second offset measures may be, for example, pre-determined distance values that are measured, between the cut plane and the respective initial catheter trajectory, along a set of surface contours defined within the internal offset surface, such that the contours intersect the cut plane.

Figure 3A:
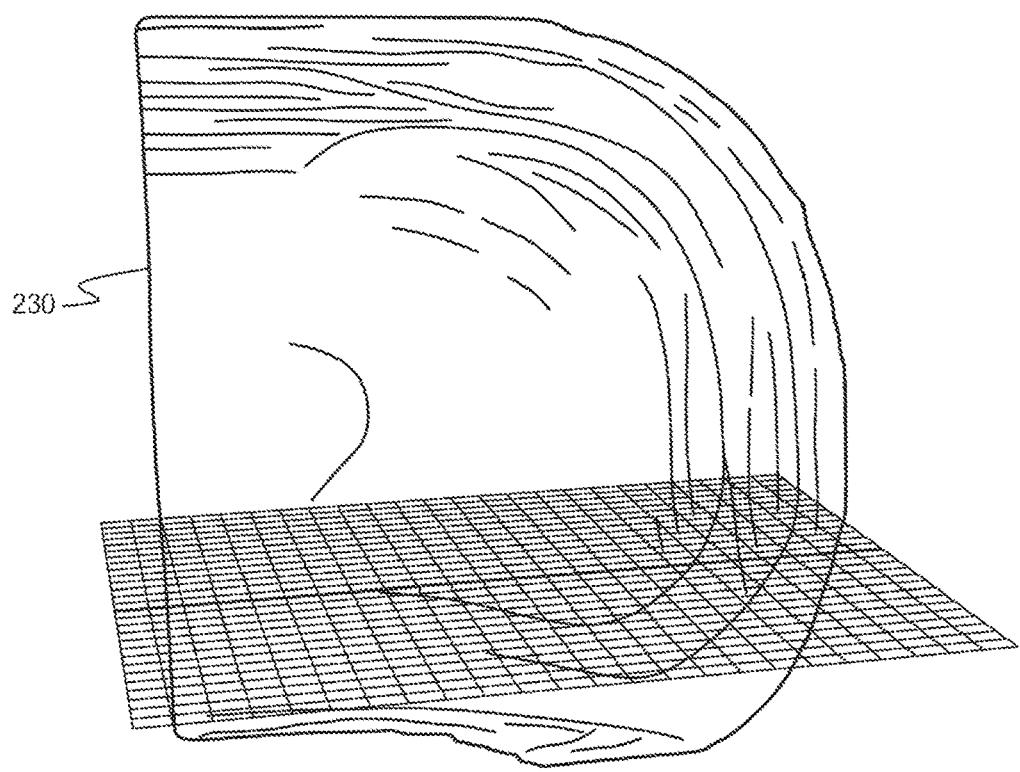
FIG. 3A shows an image of an example imported RT structure of a surface brachytherapy applicator with the patient surface visible.

An example implementation involving the use of surface contours for controlling the spacing of catheter trajectories within the patient-facing surface of the initial digital surface brachytherapy applicator model is illustrated in FIGS. 3A, 3B, 4, 5A, 5B, 6 and 7. Referring first to FIG. 3A, a initial digital surface brachytherapy applicator model 230 for use with a radiotherapy procedure is shown, with the patient-facing surface visible. This initial digital surface brachytherapy applicator model 230 may be obtained, for example, as an RT structure exported from a treatment planning system.

Figure 3B:
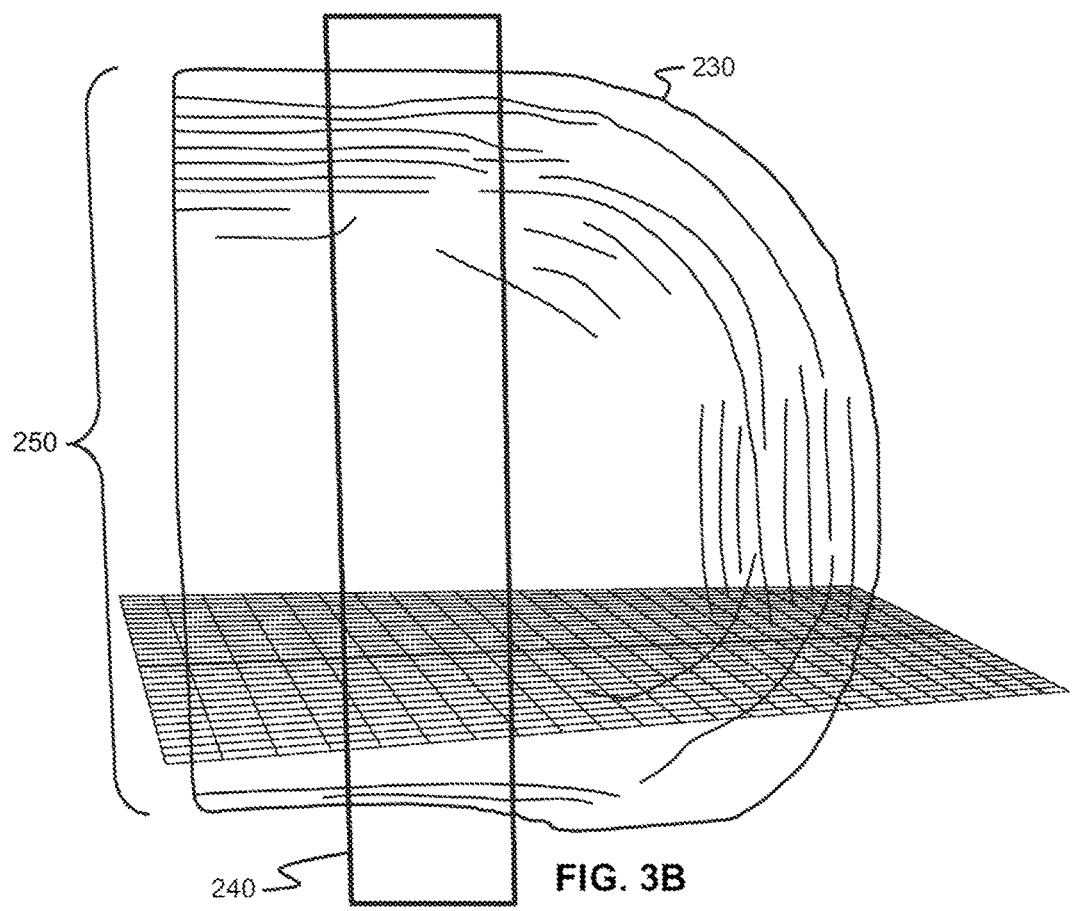
FIG. 3B shows an image of the example surface brachytherapy applicator with a cut plane, where the cut plane separates (bisects) the surface brachytherapy applicator into two sides.
Figure 4:
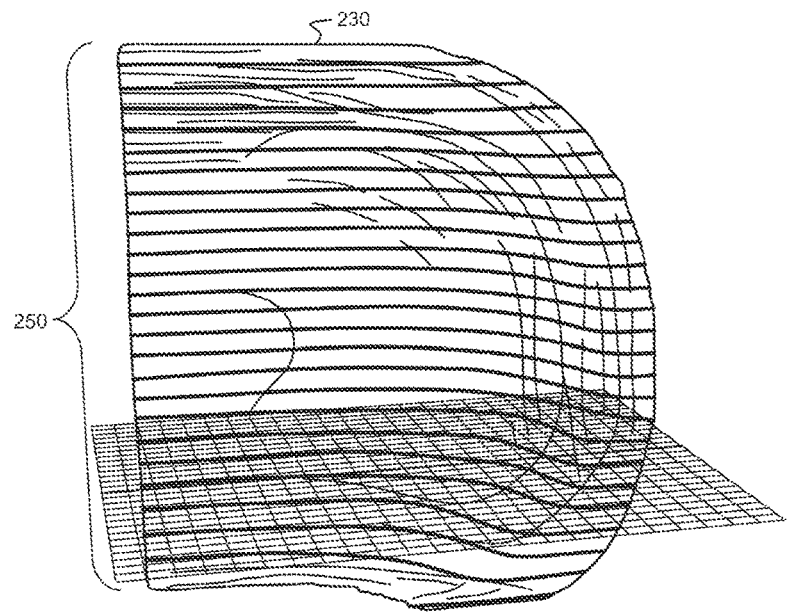
FIG. 4 shows the example surface brachytherapy applicator annotated with the set of horizontal contours.
Figures 5A, 5B:
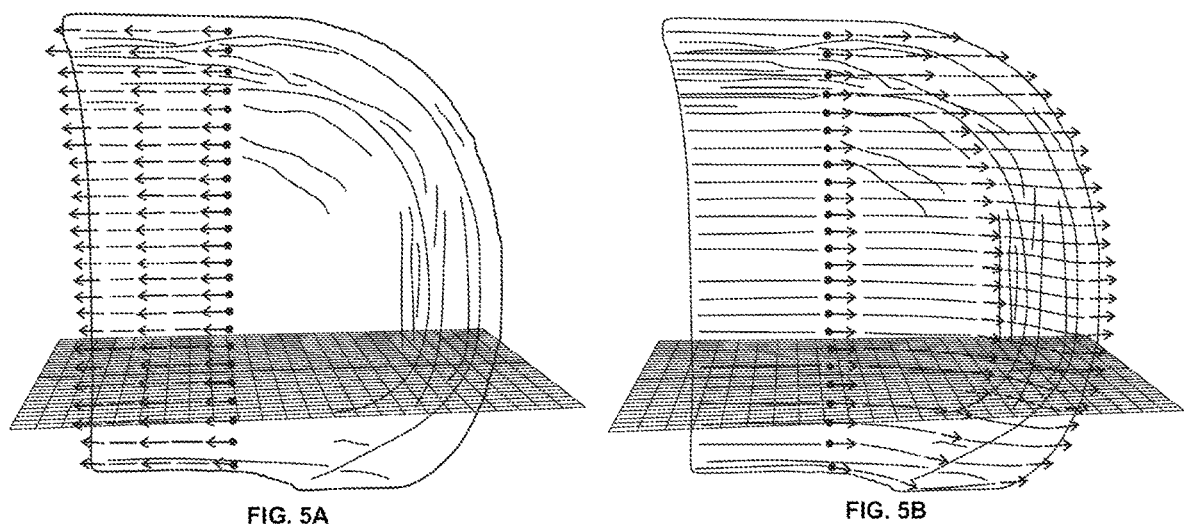
FIG. 5A shows the example surface brachytherapy applicator overlaid with an array of arrows extending along contours on the left side of the cut plane.
FIG. 5B shows the example surface brachytherapy applicator overlaid with an array of arrows extending along contours on the right side of the cut plane.

FIG. 3B shows a selected cut plane 240 bisecting the initial digital surface brachytherapy applicator model. As shown in FIG. 3B and FIG. 4, the cut plane and the initial digital surface brachytherapy applicator model are processed to generate a set of contours that reside on the patient-facing surface of the initial digital surface brachytherapy applicator model and intersect the cut plane. FIG. 4 shows an example set of contours 250 overlaid on the patient-facing surface of the initial digital surface brachytherapy applicator model 230, while FIG. 3B shows the intersection of the contours with the cut plane 240.

In the example implementation shown in FIGS. 3B and 4, the contours are generated according to a non-limiting example method based on the intersection of a set of equally spaced planes with the patient-facing surface of the initial digital surface brachytherapy applicator model 230. The set of parallel planes (not shown in the figures) are perpendicular to the cut plane 240. The intersection of the cut plane 240 and the patient-facing surface of the initial digital surface brachytherapy applicator model 230 defines a preferred orientation of the catheter tunnels. As shown in example embodiment shown FIGS. 3B and 4, the contours start and end at the opposite sides of the applicator and encompass the structure for the example initial digital surface brachytherapy applicator model shown. The contours are then shifted by the prescribed offset such that they reside within the internal offset surface (i.e. each contour is offset, along its length, in a direction parallel to a local surface normal of the patient-facing surface within the initial digital surface brachytherapy applicator model, by the prescribed offset).

It will be understood that the aforementioned method of generating contours based on the set of parallel planes is but one example of a contour-generation method and that other methods of contour generation may be employed in the alternative. For example, a surface brachytherapy applicator could be contoured slice-by-slice in a treatment planning system software until a desired structure is achieved, or outside a treatment planning system using commercially available contouring software.

With the contours shifted so that they reside within the internal offset plane, the shifted contours are employed to generate the set of catheter channel trajectories. As indicated by the arrows shown in FIG. 5A, the first set of catheter channel trajectories are generated, sequentially (serially) from the cut plane, based on distances measured along the set of contours on the left side of the cut plane. Similarly, as indicated by the arrows shown in FIG. 5B, the second set of catheter channel trajectories are generated, sequentially (serially) from the cut plane, based on distances measured along the set of contours on the right side of the cut plane.

Figure 6:
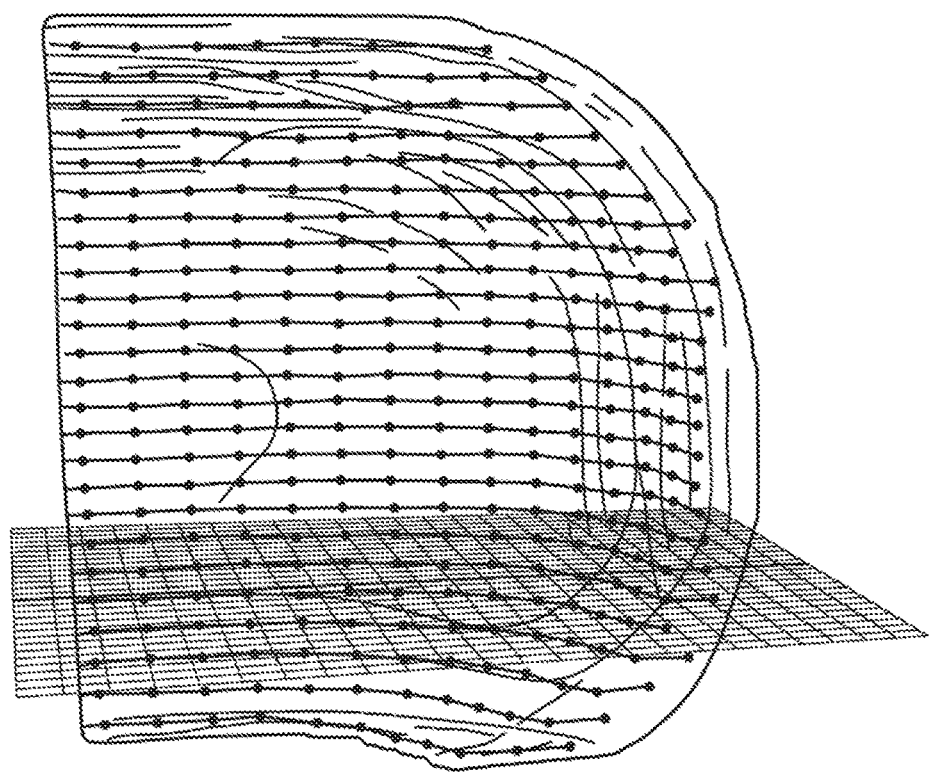
FIG. 6 shows the example surface brachytherapy applicator annotated with a series of dots extending, along the contours, from either side of the cut plane, such that the dots, along a given contour, are equidistant and define location for the generation of trajectories (in the vertical direction).
Figure 7:
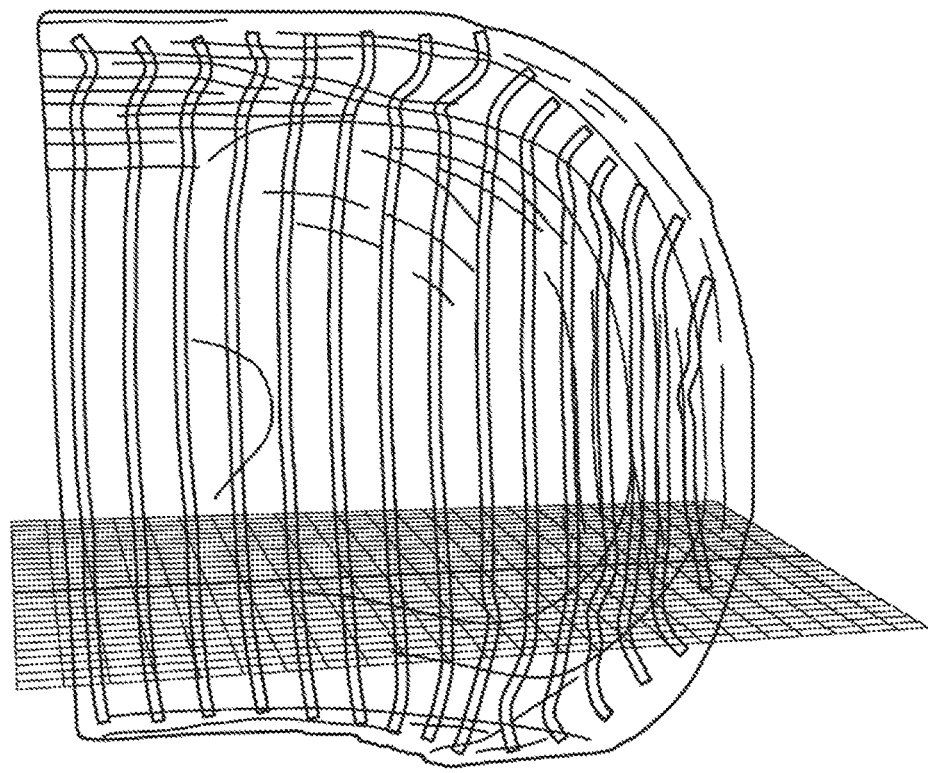
FIG. 7 shows a modified example surface brachytherapy applicator that includes catheter channels defined based on the array of dots shown in FIG. 6. The cylinders represent the catheter channels and the 'X' marks represent the points in which the horizontal contours were subdivided.

FIGS. 6 and 7 show how the contours are partitioned in equal length segments, according to the present example embodiment, by moving outward in both directions from the cut plane, to identify locations to be traversed by the set of catheter channel trajectories, thereby defining the first and second sets of catheter channel trajectories. FIG. 6 shows an array of points that are defined along each contour, while FIG. 7 demonstrates the generation of catheter channel trajectories that are defined such that adjacent points (from FIG. 6) in neighbouring contours are traversed by a common catheter channel trajectory.

According to the present example method, in order to generate locations to be traversed a catheter channel trajectory (e.g. as per the points shown in FIG. 6), an initial point is defined, for each contour, at a location separated from the cut plane, along the portion of the contour extending to the left of the cut plane, by a prescribed distance (the first offset measure previously mentioned). The set of initial points define the initial catheter channel trajectory on the left side of the cut plane.

This process is repeated to define another point, along each contour, to the left of each first initial point, thereby defining an additional catheter channel trajectory, which is then repeated to generate additional catheter channel trajectories, such that each pair of catheter channel trajectories are separated by a common distance (the constant inter-channel separation measure), as measured along the contours.

This process is repeated to define catheter channel trajectories on the other side of the cut plane (the right side in the present example). In one example implementation, a central catheter channel trajectory may be defined that lies within the cut plane, such that both the first offset measure and the second offset measure (the respective distances of the first left and first right catheter channel trajectories from the cut plane, along the contours) are equal to the constant inter-channel separation measure). In another example embodiment, the cut plane may not include a catheter channel trajectory, and the first offset measure and the second offset measure may be selected to sum to the constant inter-channel separation measure.

As noted above, by initiating the generation of catheter channel trajectories from the cut plane location, as opposed to initiating the generation of catheter channel trajectories from an edge of the initial surface brachytherapy applicator model, the effect of patient surface curvature on the curvature of the catheter channels is reduced. It will be understood that although the present example implementation involves the shifting of the contours followed by the generation of the catheter trajectories, the method may alternatively be performed by generating the catheter channel trajectories based on contours defined within the patient-facing surface, followed by the shifting of the catheter channel trajectories.

As described above, after having defined the catheter channel trajectories, the initial digital surface brachytherapy applicator model is modified to incorporate the plurality of catheter channels such that each catheter channel has a longitudinal axis defined by a respective catheter trajectory.

Figure 8A:
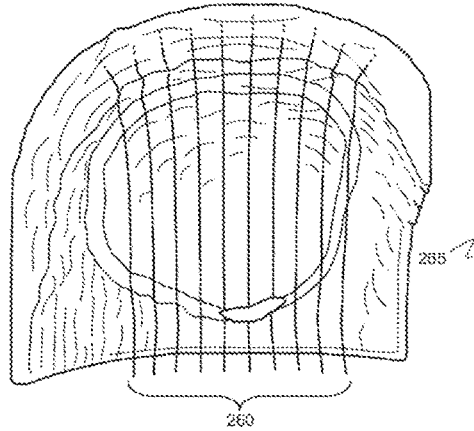
FIG. 8A shows an example user interface that accepts input from a user for defining the number of catheter trajectories, the catheter orientation, the inter-trajectory distance and the surface distance from the patient, based on a designated (selected) surface brachytherapy applicator.

FIG. 8A shows an example user interface in which a user is presented with an image of an initial digital surface brachytherapy applicator model annotated with a set of catheter channel trajectories 260 that were generated according to the aforementioned method based on a centrally-defined cut plane (not shown in the figure). The example user interface includes a set of user-definable parameters 265 that include a user-configurable inter-trajectory distance, a user-configurable number of trajectories, and a user-configurable offset of trajectories relative to the patient-facing surface of the digital surface brachytherapy applicator. The example user interface also displays the file name of a selected initial digital surface brachytherapy applicator model RT structure ("SCALP").

Figure 8B:
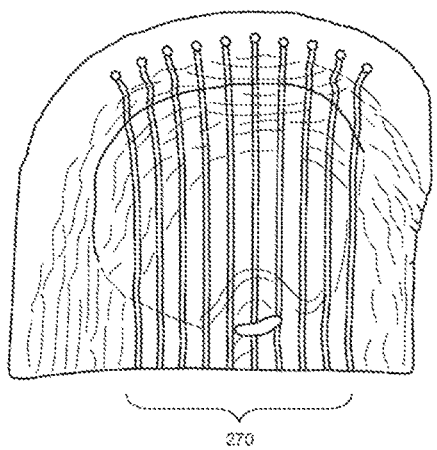
FIG. 8B shows the example user interface displaying the chosen RT structure of the surface brachytherapy applicator along with the catheter channels defined by the present example catheter channel generation algorithm.

FIG. 8B shows another example user interface view displaying the modified digital surface brachytherapy applicator model, having the catheter channels 270 defined therein, where each catheter channel is generated based on a respective catheter channel trajectory from the catheter channel trajectories shown in FIG. 8A.

In some example implementations, the cut plane may specified (defined) according to input receive by a user. For example, a user interface may permit the cut plane location to be selectable by the user, optionally by permitting the cut plane to be moved among a plurality of displayed locations relative to the initial digital surface brachytherapy applicator model.

The present inventors have found that the minimum radius of curvature of the catheter channels (i.e. the lowest local radius of curvature as measured along all catheter channels) can be increased (or maximized) by selecting a cut plane location that corresponds to an increased (or maximized, respectively) measure of curvature of the patient anatomy associated with the patient-facing surface of the initial digital surface brachytherapy applicator model. Accordingly, in one example implementation, a user may employ a user interface to select a cut plane location corresponding to a perceived location associated with a high degree of curvature of the underlying patient anatomy.

In another example embodiment, the determination of a suitable cut plane location may be at least partially automated by processing the initial digital surface brachytherapy applicator model to identify a cut plane location that maximizes a measure of curvature. This process may be guided, for example, by the selection of an initial direction by a user, such that the cut plane location is parallel to the initial direction (i.e. a user may guide the selection of a cut plane orientation in order to control the orientation of the catheter channels). A non-limiting example of a suitable measure of curvature is an integrated curvature measure, such as an integrated measure of the local radius of curvature across the curve defined by the intersection of the cut plane with the initial digital surface brachytherapy applicator model.

In another example embodiment, a plurality of modified digital surface brachytherapy applicator models may be computed, with each modified digital surface brachytherapy applicator model having a different trial cut plane location associated therewith, and the modified digital surface brachytherapy applicator model satisfying a curvature-related constraint, such as a maximized minimal local radius of curvature across all catheter channels, may be selected as a final optimized digital surface brachytherapy applicator model for fabrication and clinical use.

In some example embodiments, after having generated a modified digital surface brachytherapy applicator model having a set of catheter channels formed therein, the set of catheter channels (or catheter channel trajectories associated therewith) may be processed to identify one or more regions having a radius of curvature less than a threshold. Such a region may be displayed on a user interface, thereby alerting the user to the presence of the region. In one example implementation, the local curvature of the catheter channel may be adjustable according to input provided by a user, such that the modified digital surface brachytherapy applicator model may be refined according to the input received from the user. Upon determining that the input received by the user results in a curvature change such that the curvature of the given catheter channel over the region exceeds the threshold, an indication (e.g. on the user interface) may be provided to the user that the threshold is exceeded.

Figure 9A:
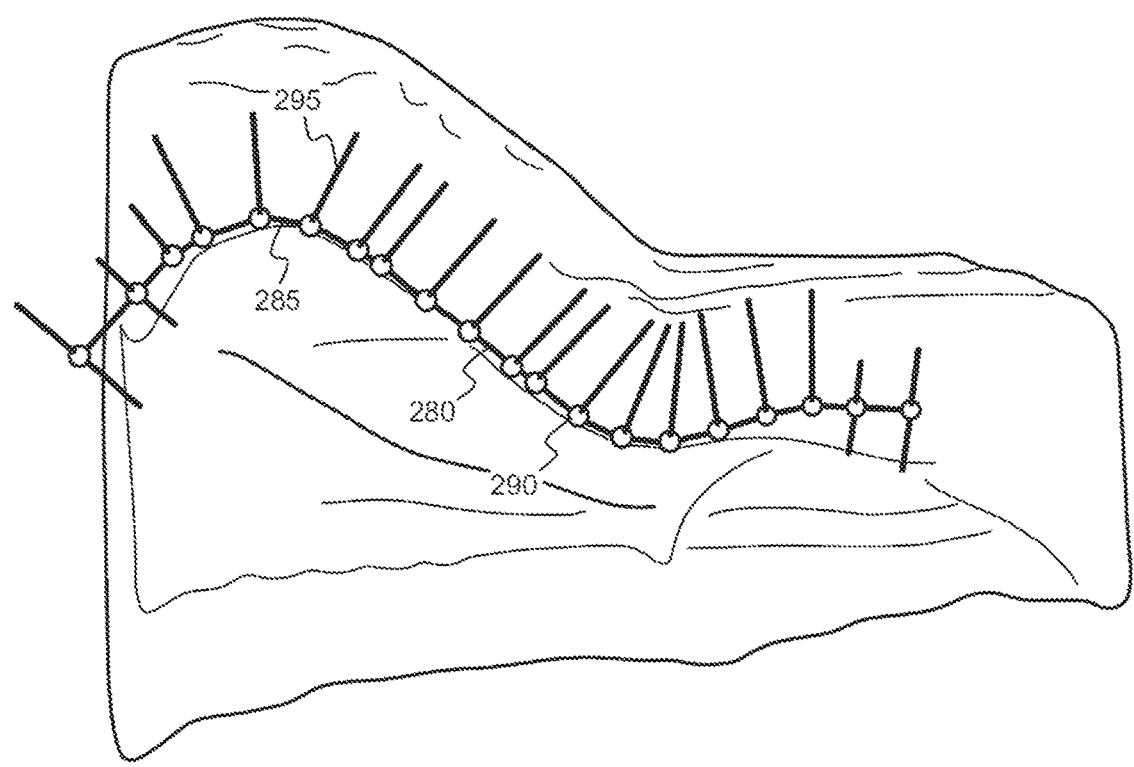
FIG. 9A illustrates an example embodiment in which a given catheter trajectory of the surface brachytherapy applicator is shown with highlighted regions having a radius of curvature that is less than a threshold value selected by a user (e.g. 13 mm). The catheter trajectory may be edited by a user in order to increase the local radius of curvature, for example, via the selection of one or more nodes (shown as dots having normal lines extending therefrom).
Figure 9B:
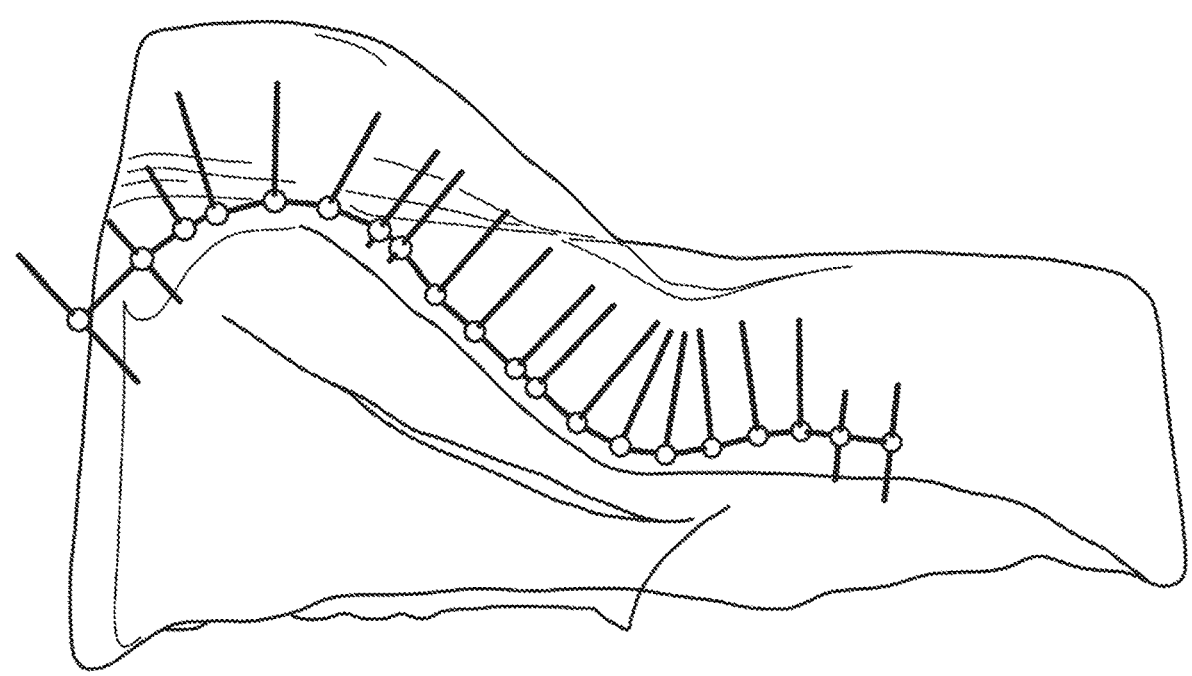
FIG. 9B shows the catheter trajectory of FIG. 9A after a user has edited the trajectory such that the local radius exceeds the radius of curvature threshold. In one example embodiment, by manually moving nodes having a radius of curvature below the threshold, the trajectory can be adjusted such that the radius of curvature exceeds threshold value, thereby facilitating safe passage of the radiation source through a catheter.

In one example embodiment, the local curvature of a catheter channel may be adjustable by a user by repositioning of one or more nodes displayed along a region of the catheter channel. Such an example embodiment is illustrated in FIGS. 9A and 9B. In FIG. 9A, a modified digital surface brachytherapy applicator model is shown with a selected catheter channel displayed. The selected catheter channel is shown with a outline over regions 280 where the local radius of curvature exceeds a threshold and an outline over regions 285 where the local radius of curvature is less than the threshold. The local radius of curvature of the catheter channel is adjustable (editable) by a user by selecting one or more nodes (circles) and providing input to modify the node position. When the local radius of curvature associated with a given node has been modified so that it exceeds the threshold, the local region is changed in shade. FIG. 9B shows the selected catheter channel after the nodes have been modified such that the local radius of curvature exceeds the threshold over the full extend of the catheter channel.

In one example embodiment, one or more catheter channels or catheter channel trajectories of the modified digital surface brachytherapy applicator model may be adjusted automatically. For example, a given catheter channel, such as the catheter channel shown in FIG. 9A, may be processed to identify one or more nodes having a local radius of curvature that is less than a threshold. For a given identified node, nodes including one or more of (i) the given node and (ii) one or more additional nodes surrounding the given identified node may be modified in position in order to increase the local radius of curvature. For example, the node in the center of the segment for which the radius of curvature is lower than the threshold may be initially selected for adjustment. If the radius of curvature cannot be amended by moving this node within a prescribed constraint (e.g. ±1 mm following an established step-size), then both the central node and one or more adjacent nodes may be collectively adjusted.

A constraint may be placed on the maximum modifiable range of any node (e.g. movable within ±1 mm in the direction perpendicular to the surface of the applicator (normal on the tangent of the trajectory curve)), and the node position may be modifiable according to a selected step size (e.g. 0.1 mm or 0.01 mm). In one example implementation, the nodes may be adjustable provided that the mean displacement of the adjusted nodes satisfies a constraint, such as being within ±1 mm.

Figure 10:
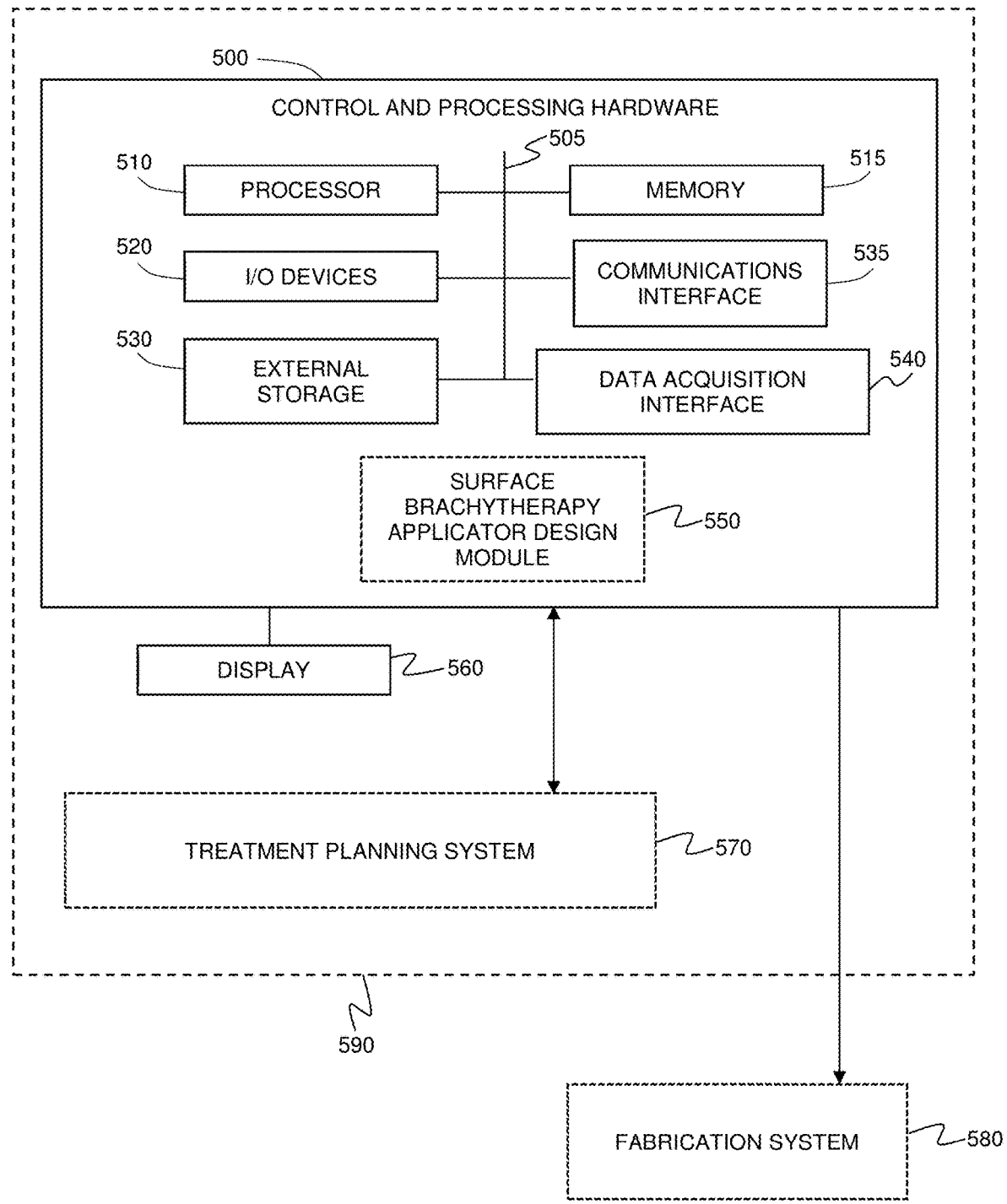
FIG. 10 is a schematic of an example system for generating a digital model of a custom surface brachytherapy applicator.

Referring now to FIG. 10, an example schematic of a system for generating a digital model of a custom surface brachytherapy applicator is shown. Control and processing hardware 500 is integrated with or connectable to a treatment planning system 570, and performs digital of a digital surface brachytherapy applicator model and may include a processor 510, a memory 515, a system bus 505, one or more input/output devices 520, and a plurality of optional additional devices such as communications interface 535, display 525, external storage 530, and data acquisition interface 540. In one example implementation, the display 560 may be employed to provide a user interface for displaying images of the digital surface brachytherapy applicator model and/or for facilitating input to control the operation of the system 500. As shown in FIG. 10, the display and/or the treatment planning system 570 may be directly integrated into a control and processing device, as shown at 590 (for example, as an embedded display), or may be provided as an external device (for example, an external monitor). The control and processing system 500 may be connected to a fabrication system 580 (such as, but not limited to, a 3D printer) for fabricating a custom surface brachytherapy applicator according to a designed digital surface brachytherapy applicator model.

The methods described herein, including the initial design of the digital surface brachytherapy applicator model and the refinement of the digital surface brachytherapy applicator model for curvature reduction, can be implemented via processor 510 and/or memory 515. As shown in FIG. 10, executable instructions represented as surface brachytherapy applicator design model 550 are processed by control and processing hardware 500 to generate the digital surface brachytherapy applicator model. Such executable instructions may be stored, for example, in the memory 515 and/or other internal storage. The control and processing hardware 500 may be interfaced with a treatment planning system 570, for example, to facilitate the performing of dose calculations and the exporting of relevant RT DICOM elements, including RT structures associated with the initial surface brachytherapy applicator model, as described above.

The methods described herein can be partially implemented via hardware logic in processor 510 and partially using the instructions stored in memory 515. Some embodiments may be implemented using processor 510 without additional instructions stored in memory 515. Some embodiments are implemented using the instructions stored in memory 515 for execution by one or more microprocessors. Thus, the disclosure is not limited to a specific configuration of hardware and/or software.

It is to be understood that the example system shown in the figure is not intended to be limited to the components that may be employed in a given implementation. For example, the system may include one or more additional processors. Furthermore, one or more components of control and processing hardware 500 may be provided as an external component that is interfaced to a processing device. Furthermore, although the bus 505 is depicted as a single connection between all of the components, it will be appreciated that the bus 505 may represent one or more circuits, devices or communication channels which link two or more of the components. For example, the bus 505 may include a motherboard. The control and processing hardware 500 may include many more or less components than those shown.

Some aspects of the present disclosure can be embodied, at least in part, in software, which, when executed on a computing system, transforms an otherwise generic computing system into a specialty-purpose computing system that is capable of performing the methods disclosed herein, or variations thereof. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

It will be understood that the example surface brachytherapy applicator design workflow and system described above is intended to provide a non-limiting example embodiment. The workflow and/or system may be modified or adapted without departing from the intended scope of the present disclosure.

For example, while the example workflow and system involves the use of a treatment planning system and a separate surface brachytherapy applicator design system, these two systems may be integrated into a common system for integrated design of the initial surface brachytherapy applicator, the design of the surface modified brachytherapy applicator having integrated catheter channels, and the processing of the dose calculation and treatment plan generation, as shown by 590 in FIG. 10. Furthermore, although the preceding example embodiments pertained to the design of a surface brachytherapy applicator, the systems and methods described above may be adapted for the design of brachytherapy devices associated with other modalities, such as, but not limited to, intracavitary brachytherapy and interstitial brachytherapy.

A custom surface brachytherapy applicator can be manufactured according to many different example methods and is particularly well-suited to automated fabrication methods such as 3D printing. 3D printing is a specific form of additive manufacturing. One of the most common methods of 3D printing is fused deposition modeling (FDM). This process has recently has become widely accessible at low cost, such as MakerBot devices. 3D printing involves a fabrication process that uses a CAD model as input to create a 3D physical model by applying many successive layers of the chosen material at a high resolution, such as a resolution of 100 micrometers, although the system can use other resolutions and capabilities.

As explained above, the preceding example embodiments have been developed to address the problems associated with conventional approaches to surface brachytherapy application design, including problems associated with cumbersome manual steps and problems associated with excessive curvature of catheter channels that can be caused by anatomical curvature of the patient.

The present example embodiments that involve automation and are compatible with three-dimensional printing may be beneficial, for example, in improving constancy of the source-to-surface distance and inter-trajectory distance of the source trajectories so that its production does not depend on the manual technical skills of the staff involved. The ability to generate equidistant source trajectories perpendicular to the curved surface of the patient with a constant surface distance, in an automated fashion, may be beneficial in significantly reducing the time of designing the applicator from several hours to minutes, when compared to traditional manual techniques (e.g. using Freiburg flap, immobilization masks, or wax moulds).

Moreover, the methods disclosed herein may be beneficial in facilitating the choice, by medical physicists, of a preferred source-to-surface distance and inter-trajectory distance of the source trajectories without having to rely on a stock of many different costly applicators. Indeed, by digitally changing source-to-surface distance and inter-trajectory distance through a user interface, the cost of designing a surface brachytherapy applicator may be significantly reduced to the absence of a need for numerous excessive physical applicators that would be required for these features using conventional methods.

Furthermore, the present example methods that permit the digital adjustment of catheter channels prior to fabrication may be beneficial in rapidly and inexpensively facilitating convergence to a final surface brachytherapy applicator design. Such a capability allows medical physicists to correct for extreme trajectory curvatures that could potentially be hazardous for the passing of the source through a catheter, allowing improved quality and safety of surface brachytherapy RT treatment plans that would otherwise be unfeasible, ensuring patients receive the optimal cancer treatment modality.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A method of generating a digital model of a custom surface brachytherapy applicator, the method comprising:
   a) obtaining an initial digital surface brachytherapy applicator model, wherein the initial digital surface brachytherapy applicator model comprises a patient-facing surface;
   b) identifying a cut plane for bisecting the initial digital surface brachytherapy applicator model;
   c) processing the initial digital surface brachytherapy applicator model to incorporate a plurality of catheter channels, thereby obtaining a modified digital surface brachytherapy applicator model, wherein the plurality of catheter channels are incorporated such that:
      a first set of catheter channels are spatially distributed, relative to the cut plane, on a first side of the cut plane; and
      a second set of catheter channels are spatially distributed, relative to the cut plane, on a second side of the cut plane;
   wherein the cut plane is identified by:
      processing the initial digital surface brachytherapy applicator model to determine, for each trial cut plane of a plurality of trial cut planes, a curvature measure associated with a curve defined by an intersection of the trial cut plane with the patient-facing surface of the initial digital surface brachytherapy applicator model; and
      selecting the trial cut plane for which the curvature measure satisfies curvature criteria.

2. The method according to claim 1 wherein processing the initial digital surface brachytherapy applicator model to incorporate the plurality of catheter channels comprises:
   processing the initial digital surface brachytherapy applicator model to define, relative to the patient-facing surface of the initial digital surface brachytherapy applicator model, a plurality of catheter trajectories, wherein the plurality of catheter trajectories are defined such that:
      a first set of catheter trajectories are spatially distributed, relative to the cut plane, on the first side of the cut plane; and
      a second set of catheter trajectories are spatially distributed, relative to the cut plane, on the second side of the cut plane; and
   wherein the plurality of catheter trajectories are defined such that they reside within an internal offset surface recessed, within the initial digital surface brachytherapy applicator model, relative to the patient-facing surface, by a prescribed offset, such that the plurality of catheter trajectories reside within the initial digital surface brachytherapy applicator model; and
   modifying the initial digital surface brachytherapy applicator model to incorporate the plurality of catheter channels such that each catheter channel has a longitudinal axis defined by a respective catheter trajectory.

3. The method according to claim 2 wherein the first set of catheter trajectories are defined, relative to the cut plane, by:
   defining an initial first catheter trajectory that resides within the internal offset surface adjacent to the cut plane, on the first side of the cut plane, and is spatially offset, along a length thereof, from the cut plane by a first offset measure defined within the internal offset surface; and
   defining a plurality of additional first catheter trajectories on the first side of the cut plane, such that each pair of neighbouring first catheter trajectories are spatially offset, within the internal offset surface, by a constant inter-channel separation measure; and
   wherein the second set of catheter trajectories are defined, relative to the cut plane, by:
   defining an initial second catheter trajectory that resides within the internal offset surface adjacent to the cut plane, on the second side of the cut plane, and is spatially offset, along a length thereof, from the cut plane by a second offset measure defined within the internal offset surface; and
   defining a plurality of additional second catheter trajectories on the second side of the cut plane, such that each pair of neighbouring second catheter trajectories are spatially offset, within the internal offset surface, by the constant inter-channel separation measure.

4. The method according to claim 3 wherein the plurality of catheter trajectories further comprises a central catheter trajectory defined at an intersection of the cut plane with the internal offset surface, and wherein the first offset measure and the second offset measure are both equal to the constant inter-channel separation measure.

5. The method according to claim 3 wherein a sum of the first offset measure and the second offset measure is equal to the constant inter-channel separation measure.

6. The method according to claim 3 wherein the first offset measure, the second offset measure and the constant inter-channel separation measure are determined along a set of contours defined within the internal offset surface, wherein each contour intersects the cut plane, such that:
   the initial first catheter trajectory, residing adjacent to the cut plane, on the first side of the cut plane, is spatially offset from the cut plane, along each contour within the internal offset surface, by the first offset measure;
   each pair of neighbouring first catheter trajectories are spatially offset, along each contour within the internal offset surface, by the constant inter-channel separation measure;
   the initial second catheter trajectory, residing adjacent to the cut plane, on the second side of the cut plane, is spatially offset from the cut plane, along each contour within the internal offset surface, by the second offset measure; and
   each pair of neighbouring second catheter trajectories are spatially offset, along each contour within the internal offset surface, by the constant inter-channel separation measure.

7. The method according to claim 6 wherein the set of contours are defined by intersections of a set of parallel planes with the internal offset surface.

8. The method according to claim 7 wherein the set of parallel planes are perpendicular to the cut plane.

9. The method according claim 1 wherein cut plane is identified based on input from a user.

10. The method according to claim 1 wherein the curvature measure provides a measure of curvature along the curve, and wherein the curvature criteria is satisfied by the trial cut plane having a maximized measure of curvature.

11. The method according to claim 1 further comprising receiving user input identifying a preferred direction, and wherein the plurality of trial cut planes are defined such that the plurality of trial cut planes are parallel to the preferred direction.

12. The method according to claim 1 wherein the cut plane is a first test cut plane, and wherein the modified digital surface brachytherapy applicator model is a first modified digital surface brachytherapy applicator model, the method further comprising:
   performing steps b) and c) for a plurality of additional test cut planes, thereby obtaining a plurality of additional modified digital surface brachytherapy applicator models;
   processing the first modified digital surface brachytherapy applicator model and the additional modified digital surface brachytherapy applicator models to select a modified digital surface brachytherapy applicator model satisfying curvature criteria.

13. The method according to claim 12 wherein the curvature criteria is assessed by:
   processing each modified digital surface brachytherapy applicator model to determine a minimum radius of curvature of all catheter channels incorporated therein; and
   selecting the modified digital surface brachytherapy applicator model having the largest associated minimum radius of curvature.

14. The method according to claim 1 further comprising:
   determining a region over which a local radius of curvature of a given catheter channel is less than a threshold;
   displaying, on a user interface, an image identifying the region such that a curvature of the region of the given catheter channel is adjustable according to input provided by a user; and
   refining the modified digital surface brachytherapy applicator model according to the input received from the user.

15. The method according to claim 14 wherein the curvature of the region of the given catheter channel is adjustable by repositioning of one or more nodes.

16. The method according to claim 14 further comprising determining that the input received by the user results in a curvature change such that the curvature of the given catheter channel over the region exceeds the threshold; and
   providing an indication on the user interface that the threshold is exceeded.

17. A method of generating a custom surface brachytherapy applicator, the method comprising:
   generating a digital model of a custom surface brachytherapy applicator according to the method of claim 1; and
   fabricating the custom surface brachytherapy applicator according to the modified digital surface brachytherapy applicator model.

18. A system for generating a digital model of a custom surface brachytherapy applicator, the system comprising:
   a processing system comprising at least one processor and memory operatively coupled to the at least one processor, wherein the memory comprises instructions executable by the at least one processor for performing operations comprising:
   obtaining an initial digital surface brachytherapy applicator model, wherein the initial digital surface brachytherapy applicator model comprises a patient-facing surface;
   identifying a cut plane for bisecting the initial digital surface brachytherapy applicator model;
   processing the initial digital surface brachytherapy applicator model to incorporate a plurality of catheter channels, thereby obtaining a modified digital surface brachytherapy applicator model, wherein the plurality of catheter channels are incorporated such that:
      a first set of catheter channels are spatially distributed, relative to the cut plane, on a first side of the cut plane; and
      a second set of catheter channels are spatially distributed, relative to the cut plane, on a second side of the cut plane;
   wherein the cut plane is identified by:
      processing the initial digital surface brachytherapy applicator model to determine, for each trial cut plane of a plurality of trial cut planes, a curvature measure associated with a curve defined by an intersection of the trial cut plane with the patient-facing surface of the initial digital surface brachytherapy applicator model; and
   selecting the trial cut plane for which the curvature measure satisfies curvature criteria.

19. A method of generating a digital model of a custom surface brachytherapy applicator, the method comprising:

a) obtaining an initial digital surface brachytherapy applicator model, wherein the initial digital surface brachytherapy applicator model comprises a patient-facing surface;
b) identifying a cut plane for bisecting the initial digital surface brachytherapy applicator model;
c) processing the initial digital surface brachytherapy applicator model to incorporate a plurality of catheter channels, thereby obtaining a modified digital surface brachytherapy applicator model, wherein the plurality of catheter channels are incorporated such that:
  a first set of catheter channels are spatially distributed, relative to the cut plane, on a first side of the cut plane; and
  a second set of catheter channels are spatially distributed, relative to the cut plane, on a second side of the cut plane;
wherein the cut plane is a first test cut plane, and wherein the modified digital surface brachytherapy applicator model is a first modified digital surface brachytherapy applicator model, the method further comprising:
  performing steps b) and c) for a plurality of additional test cut planes, thereby obtaining a plurality of additional modified digital surface brachytherapy applicator models;
  processing the first modified digital surface brachytherapy applicator model and the additional modified digital surface brachytherapy applicator models to select a modified digital surface brachytherapy applicator model satisfying curvature criteria.

20. A method of generating a digital model of a custom surface brachytherapy applicator, the method comprising:
  obtaining an initial digital surface brachytherapy applicator model, wherein the initial digital surface brachytherapy applicator model comprises a patient-facing surface;
  processing the initial digital surface brachytherapy applicator model to incorporate a plurality of catheter channels, thereby obtaining a modified digital surface brachytherapy applicator model;
  determining a region over which a local radius of curvature of a given catheter channel is less than a threshold;
  displaying, on a user interface, an image identifying the region such that a curvature of the region of the given catheter channel is adjustable according to input provided by a user; and
  refining the modified digital surface brachytherapy applicator model according to the input received from the user.

* * * * *